United States Patent [19]

Kondo et al.

[11] Patent Number: 5,106,732
[45] Date of Patent: Apr. 21, 1992

[54] METHOD FOR ENHANCEMENT OF CHEMILUMINESCENCE

[75] Inventors: Koichi Kondo, Soraku; Takashi Sohda, Takatsuki, both of Japan

[73] Assignee: Takeda Chemical Industries, Ltd., Osaka, Japan

[21] Appl. No.: 480,064

[22] Filed: Feb. 14, 1990

[30] Foreign Application Priority Data

Feb. 14, 1989 [JP] Japan .................................. 1-34729

[51] Int. Cl.$^5$ .................. C12Q 1/28; C12Q 1/34; C07D 291/00; C07D 419/00
[52] U.S. Cl. ........................ 435/28; 435/18; 435/968; 436/826; 548/122
[58] Field of Search ............. 435/28, 18, 34, 968; 436/826; 548/122

[56] References Cited

U.S. PATENT DOCUMENTS

| | | | |
|---|---|---|---|
| 4,659,657 | 4/1987 | Harnisch et al. | 435/18 |
| 4,729,950 | 3/1988 | Kricka et al. | 435/28 |
| 4,842,997 | 6/1989 | Carter et al. | 435/6 |
| 4,950,588 | 8/1990 | Da Hagupta | 435/805 |

FOREIGN PATENT DOCUMENTS

| | | |
|---|---|---|
| 0087959 | 9/1983 | European Pat. Off. . |
| 0116454 | 8/1984 | European Pat. Off. . |
| 0210449 | 2/1987 | European Pat. Off. . |
| 0296752 | 6/1988 | European Pat. Off. . |
| 58-158542 | 9/1983 | Japan . |

*Primary Examiner*—Christine Nucker
*Assistant Examiner*—David R. Preston
*Attorney, Agent, or Firm*—Wegner, Cantor, Mueller & Player

[57] ABSTRACT

A method for enhancing chemiluminescence which uses a heterocyclic compound of the formula:

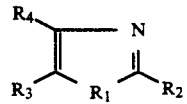

wherein $R_1$ is an oxygen or sulfur atom or an imino group optionally substituted by 4-hydroxyphenyl, and $R_2$, $R_3$ and $R_4$ are a hydrogen or halogen atom, an optionally substituted hydrocarbon residue, a heterocyclic group or the like in a luminescence system.

12 Claims, 1 Drawing Sheet

FIG. 1

METHOD FOR ENHANCEMENT OF CHEMILUMINESCENCE

BACKGROUND OF THE INVENTION

1. Field of the Invention

This invention relates to a method for enhancing chemiluminescence.

Particularly, this invention relates to a method for detecting a chemically luminous substance, especially to a method for enhancing chemiluminescence which can achieve an improvement of sensitivity of immunological quantitative analysis, enzymatic quantitative analysis or the like based on the quantitative analysis of chemically luminous substance and measuring of chemiluminescence.

2. Description of the Prior Art

Analytical method based on chemical luminous reaction has a possibility to become an extremely high-sensitive method for detecting a chemical substance and has been intensively studied. Attention has been focused on to this analytical method especially in the field of immunological analysis, to which various kinds of techniques have been tried.

In the immunological analysis, a method using radioactive isotope (RIA) as a label has been developed at first, which however shows the disadvantages due to the use of radioactive isotope, namely, short half-valued period, bio-hazard problem and occasionally insufficient sensitivity. And then, a detecting method by colorimetric analysis or fluorescence analysis such as enzyme-immunological analysis using enzyme as a label has been developed for overcoming the disadvantages accompanied by RIA. However, development of new techniques was sought to achieve improvement on sensitivity. Among the new techniques, a method utilizing chemiluminescence as detecting means is expected to be the most sensitive method and accordingly has been intensively studied.

Immunochemical analysis methods utilizing chemical luminous reaction are generally classified into the following 4 methods [Akio Tsuji et al., Peptide, Nucleic Acid and Enzyme, Extra Issue, Vol. 31, pages 255-263 (1988)]:

(1) A method labeling a chemically luminous substance such as luminol, isoluminol, acridinium derivative, etc., as a label compound on antibody or antigen.

(2) A method utilizing chemical luminous reaction for measuring enzyme activity in the enzyme immunological analysis (EIA) labeling enzyme on antibody or antigen.

(3) A homogeneous immunological analysis utilizing phenomenon of decrease of coenzyme activity by antigen-antibody reaction in which coenzyme, namely, NAD or ATP is labeled.

(4) Enzyme immunological analysis utilizing biological luminous reaction.

Among these methods, the method (1) involves some problems. That is, the sensitivity can not be improved as expected due to decline of luminous quantum yield caused by chemical combination of luminous substance, and measuring in a very short time of chemiluminescence is extremely difficult.

Improvement of sensitivity by the above method (3) can not be expected, and the method (4) can not be generalized due to use of specific enzyme in many cases.

On the other hand, improvement of sensitivity by the above method (2) can be expected, because the chemically luminous substance exists in a free form in the solution and the luminous reaction is catalyzed by labeled enzyme. In this case, however, the luminous reaction continued generally for a very short time and could not result in substantial improvement of the sensitivity.

Recently, it was found that total luminous quantum by chemical luminous reaction can be extremely improved by coexistence of a third compound in a chemical luminous reaction system. That is, G. H. G. Thorpe and L. J. Kricka reported a group of compounds improving a luminous reaction of luminol using peroxidase as a catalyst in their general remarks in "Methods in Enzymology", Vol. 133, pages 331-353 (1986, Academic Press, N.Y.). As described on page 335, strong activity as an enhancer was recognized for 6-hydroxybenzothiazole and phenol derivatives. The use of these enhancers can delay chemical luminous reaction and increase chemical luminous quantum and therefore enable solving such a problem that the chemical luminous reaction must be checked within a few seconds, thereby making the condition for measurement less restricted.

The following enhancers have been found:
(1) 6-Hydroxybenzothiazole
(2) Phenol derivatives such as p-iodophenol or naphthol derivatives (Japanese Patent Kokai No. 171,839/1984)
(3) Ammonia and water-soluble organic amines (Japanese Patent Kokai No. 124,446/1987)
(4) Aromatic amine compounds (Japanese Patent Kokai No. 54,453/1986)
(5) Amino acids having cyclic group
(6) Fluorescence substances.

Among these enhancers, the above (1) and p-iodophenol in the above (2) were selected as the superior ones.

However, it was necessary to find a better enhancer for improving sensitivity of the analysis. That is, if sensitivity could be successfully improved, very small amount of a biologically active substance in a living body can be easily detected, and accordingly any substance which has not been able to be measured due to its too small amount will be able to be detected. Then, it will be possible to know a normal value of a very small amount of a substance, and also to detect an increase of concentration of the substance at an early stage of a disease, and accordingly to make a diagnosis of the disease at an early stage. And further, it will be possible to detect a substance which further decreases in accordance with a disease, and a new method to make a diagnosis of a disease will be developed. Very useful means for managing recuperation of a disease will also be developed. These methods can be utilized not only in diagnosis of a disease, but also in a field where microanalysis is essential such as environmental analysis, and further in detection of a bioactive substance and elucidation of movement of a substance in a living body.

SUMMARY OF THE INVENTION

This invention relates to a method for enhancing chemiluminescence, which comprises using a compound of the general formula (I):

[wherein $R_1$ is an oxygen or sulfur atom or an imino group which may be substituted by 4-hydroxyphenyl, $R_2$, $R_3$ and $R_4$ are each a hydrogen atom, a halogen atom, a hydrocarbon residue which may be substituted or a heterocyclic group which may be substituted, or $R_3$ and $R_4$ taken together form a di-valent group (sometimes hereinafter known as a "divalent bridge group") which is identified by the formula:

(wherein, $R_5$ is a hydrogen atom or a hydroxy group), provided that when $R_1$ is an oxygen or sulfur atom or an imino group, $R_4$ is a 4-hydroxyphenyl group and when $R_1$ is 4-hydroxyphenylimino group, $R_4$ is a hydrogen atom] in a luminescence system consisting of a chemically luminous substance, an oxidizing agent and a peroxidase. No significance is to be given to any angle of the lines extending from the phenylene nucleus and from the methylene group.

Thus, a characteristic feature of the present invention resides in permitting the compound of the general formula (I) to co-exist in the known luminescence system.

DESCRIPTION OF PREFERRED EMBODIMENTS

In the above general formula (I), the halogen atom may be fluorine, chlorine, bromine or iodine. The hydrocarbon moiety in the "hydrocarbon residue which may be substituted" may be alkyl group (preferably $C_{1-10}$ alkyl group), alkenyl group (preferably $C_{2-10}$ alkenyl group), aryl group (preferably $C_{6-14}$ aryl group), or aralkyl group (preferably $C_{7-19}$ aralkyl group). The suitable heterocyclic group may be 5- to 7-membered heterocyclic group, for example, 5- to 7-membered heterocyclic group containing a sulfur atom, nitrogen atom or oxygen atom, 5- to 6-membered heterocyclic group containing 2 to 4 nitrogen atoms, 5- to 6-membered heterocyclic group containing 1 to 2 nitrogen atom(s) and a sulfur atom, and these heterocyclic groups may be condensed with a 6-membered ring containing 1 or 2 nitrogen atom(s), a benzene ring or a 5-membered ring containing a sulfur atom.

The $C_{1-10}$ alkyl group may be methyl, ethyl, propyl, isopropyl, butyl, isobutyl, sec-butyl, tert-butyl, pentyl, isopentyl, neopentyl, hexyl, heptyl, octyl, nonyl, decyl or the like. The $C_{2-10}$ alkenyl group may be, for example, allyl, 2-butenyl, 2-pentenyl, 3-hexenyl, 2-cyclopentenyl, 2-cyclohexenyl, or the like. The suitable aryl group may be the one of 6 to 14 carbon atoms, for example, phenyl, anthryl, biphenyl or the like. The suitable $C_{7-19}$ aralkyl group may be a combination of a $C_{6-14}$ aryl group and a $C_{1-4}$ alkyl group, for example, benzyl, phenethyl or the like.

Suitable examples of the above 5- to 7-membered heterocyclic groups may be 2-pyridyl, pyrimidyl, pyrazinyl, pyridazinyl, pyrazolyl, imidazolyl, thiazolyl, oxazolyl, pyrido[2,3-b]pyrimidyl, benzopyranyl, 1,8-naphthyridinyl, quinolyl, thieno[2,3-b] pyridyl, tetrazolyl, thiadiazolyl, oxadiazolyl, triazinyl, triazolyl, thienyl, pyrrolyl, pyrrolinyl, furyl, pyrrolidinyl, benzothienyl, indolyl, imidazolidinyl, piperidyl, piperidino, piperazinyl, morpholinyl, morpholino, or the like.

The hydrocarbon residue represented by $R_2$, $R_3$ and $R_4$ may have 1 to 3 optional substituent(s) such as a halogen (e.g., fluorine, chlorine, bromine or iodine), hydroxy group, a $C_{1-6}$ alkoxy group, an amino group which may be substituted with a $C_{1-6}$ alkyl (e.g., dimethylamino, diethylamino, dipropylamino, etc.), an amino group substituted with an acyl group derived from an organic carboxylic acid (e.g., $C_{1-10}$ alkanoyl, etc.) (e.g., acetylamino, propionylamino, benzoylamino, etc.), a carbamoyl group which may be substituted with a $C_{1-6}$ alkyl group (e.g., dimethylcarbamoyl, ethylcarbamoyl, dipropylcarbamoyl, etc.), a mono- or dialkoxyphosphoryl group, an esterified carboxy group, for instance, an alkoxycarbonyl group, preferably a $C_{1-6}$ alkoxycarbonyl group (e.g., methoxycarbonyl, ethoxycarbonyl, propoxycarbonyl, butoxycarbonyl, etc.), an aryloxycarbonyl group, preferably a $C_{6-14}$ aryloxycarbonyl group (e.g., phenoxycarbonyl, etc.), an aralkyloxy carbonyl group, preferably a $C_{7-19}$ aralkyloxycarbonyl group (e.g., benzyloxycarbonyl, etc.), and the like.

Examples of substituents on the heterocyclic group which may be substituted of $R^2$, $R^3$ and $R^4$ are a halogen atom (e.g., fluorine, chlorine, bromine or iodine), a $C_{1-6}$ alkyl group, a halogenated $C_{1-6}$ alkyl group substituted by the above mentioned halogen, hydroxy group, a $C_{1-6}$ alkoxy group, a $C_{1-10}$ acyl group, an amino group which may be substituted by a $C_{1-6}$ alkyl or a $C_{1-10}$ acyl (e.g., dimethylamino, diethylamino, dipropylamino, acetylamino, propionylamino or benzoylamino), a carbamoyl group which may be substituted by a $C_{1-6}$ alkyl (e.g., dimethylcarbamoyl, diethylcarbamoyl or dipropylcarbamoyl), a $C_{1-6}$ alkoxycarbonyl group (e.g., methoxycarbonyl, ethoxycarbonyl or propoxycarbonyl) or the above mentioned heterocyclic group.

The compounds represented by the formula (I) may be oxazole derivatives where $R_1$ is an oxygen atom, thiazole derivatives where $R_1$ is a sulfur atom or imidazole derivatives where $R_1$ is an imino group.

Among these derivatives, preferable compounds are the ones having 4-hydroxyphenyl group for $R_4$ and hydrogen atom, a halogen atom, a hydrocarbon residue which may be substituted, preferably an alkyl, alkenyl or aromatic group, or a heterocyclic group for $R_2$ and $R_3$. Especially, suitable derivatives are compounds where $R_2$ and $R_3$ are hydrogen atoms, compounds where $R_3$ is a hydrogen atom and $R_2$ is a lower alkyl group such as methyl group or ethyl group, compounds where $R_3$ is a hydrogen atom and $R_2$ is a halogen atom, compounds where $R_3$ is a lower alkyl group such as methyl group or ethyl group and $R_2$ is a halogen atom, compounds where $R_3$ is a halogen atom and $R_2$ is a hydrogen atom, compounds where $R_3$ is a halogen atom and $R_2$ is a lower alkyl group, compounds where $R_3$ is a pyridyl group and $R_2$ is a hydrogen atom, compounds where $R_3$ is a pyridyl group and $R_2$ is a lower alkyl group such as methyl group or ethyl group, compounds where $R_3$ is a hydrogen atom and $R_2$ is a pyridyl group, compounds where $R_3$ is a lower alkyl group ($C_{1-4}$ alkyl group) such as methyl group or ethyl group and $R_2$ is a pyridyl group, compounds where $R_3$ is a hydrogen atom and $R_2$ is an alkoxycarbonylalkyl group such as ethoxycarbonylethyl group, and the like.

And further, suitable derivatives are the compounds where $R_1$ is an imino group substituted by a 4-hydroxyphenyl group, $R_3$ is a hydrogen atom, $R_2$ and $R_4$ are each hydrogen atom, a halogen atom, an alkyl group, alkenyl group or aromatic group which may be substituted or a heterocyclic group, especially the compounds where $R_2$ and $R_4$ are hydrogen atoms, compounds where $R_2$ is a hydrogen atom and $R_4$ is a lower alkyl group such as methyl group or ethyl group, compounds where $R_2$ is a hydrogen atom and $R_4$ is a halogen atom, compounds where $R_2$ is a lower alkyl group such as methyl group or ethyl group and $R_4$ is a halogen atom, compounds where $R_2$ is a halogen atom and $R_4$ is a hydrogen atom, compounds where $R_2$ is a halogen atom and $R_4$ is a lower alkyl group such as methyl group or ethyl group, compounds where $R_2$ is a pyridyl group and $R_4$ is a hydrogen atom, compound where $R_2$ is a pyridyl group and $R_4$ is a lower alkyl group such as methyl group or ethyl group, compounds where $R_2$ is a hydrogen atom and $R_4$ is a pyridyl group, compounds where $R_2$ is a lower alkyl group such as methyl group or ethyl group and $R_4$ is a pyridyl group, compounds where $R_2$ is a hydrogen atom and $R_4$ is an alkoxycarbonylalkyl group such as ethoxycarbonylethyl group, and the like.

A further embodiment of the invention provides compounds wherein $R_3$ and $R_4$ together form the aforementioned di-valent bridging group, and $R_2$ is a hydrogen atom, a halogen atom, an alkyl, alkenyl or aromatic group which may be substituted or a heterocyclic group, especially a hydrogen atom, a halogen atom, lower alkyl group such as methyl group or ethyl group, pyridyl group or an alkoxycarbonylalkyl group such as ethoxycarbonylethyl group are also suitable derivatives.

The peroxidase used also in this invention according to the known technique may be the ones derived from various kinds of origins such as horseradish, pineapple, fig, sweet potato, broad bean, corn and the like, and especially horseradish peroxidase extracted from horseradish is suitable.

Peroxidase is used in a free form (non-labeled form) according to analysis system, but it is necessary to be bonded with an immunochemically active substance such as antigen, hapten, antibody or the like in case of immunochemical analysis using a method of the present invention.

The combination of peroxidase with an immunochemically active substance can be achieved by using the known methods. For instance, glutaraldehyde cross linking method [Immunochemistry, Vol. 6, page 43 (1969); bid. Vol. 8, page 1175 (1971)], periodic acid cross linking method [J. Histochem. Cytochem., Vol. 22, page 1084 (1974)], and especially the method using a bonding agent of the formula:

wherein, n is an integer of 0 to 5, and R is a chemical bond or 6-membered, cyclic hydrocarbon residue [Japanese Patent Kokai 149,700/ 1983] can be preferably applied.

Luminol and its derivative, lophin, lucigenin and the like have been known as chemically luminous substances.

Suitable substance may be luminol and its derivatives as described in "Methods in Encymology", vol. 57, pages 409–423 (1987), for example, luminol, isoluminol, N-(4-aminobutyl)-N-ethylisoluminol hemisuccinimide, N-(6-aminohexyl)-N-ethylisoluminol, N-ethylisoluminol or the like. Among these substances, luminol and isoluminol are preferably used.

The oxidizing agent to be used also in this invention according to the known technique may be the one which can yield luminous energy by chemical luminous reaction. For example, oxidizing agents such as hydrogen peroxide, perboric acid salt, etc., can be preferably used. And further, a system in which an oxidizing agent is indirectly produced, for example, a system in which hydrogen peroxidase is produced from glucose by using an enzyme such as glucose oxidase can be applied.

A suitable measuring system to be employed in this invention comprises
1. peroxidase or an immunochemically active substance labeled by peroxidase,
2. oxidizing agent (hydrogen peroxide or its analogue),
3. luminol or its derivative and
4. compound (I) (enhancer).

In general, peroxidase is used in chemical combination with hapten, antigen, antibody or the like. The above reagents 2, 3 and 4 are used in a fixed amount, and a condition is chosen so that a very small change of the amount of peroxidase at a low concentration brings about a large change in the amount of light produced. Chemical luminous reaction is delayed and luminous quantum is extremely enhanced by using the enhancer. Through these phenomena, it becomes possible to detect a very small amount of substance in comparison with the prior art.

The method of this invention using the compound (I) as an enhancer in the chemical luminous reaction is preferably conducted under the following conditions:

The reaction temperature may be 0° to 60° C., preferably 5° to 30° C. The pH value of a buffer to be used may be within the range from around neutral to alkaline, for instance, pH 7 to 10, preferably pH 8 to 9. Various kinds of buffers can be used as a buffer, and borate buffer, phosphate buffer, carbonate buffer, Tris buffer, etc. can be preferably used.

The concentrations of the reagents can vary in accordance with the enhancer to be used, but the following concentrations are usually preferable:

| | |
|---|---|
| (1) peroxidase | 0–1000 g/l |
| (2) oxidizing agent (hydrogen peroxide) | 1 μM–30 mM |
| (3) enhancer | 0.1 μM–10 mM |
| (4) luminous substance (luminol) | 1 μM–10 mM |

Especially, the concentration of 0 to 1 μg/liter for the above (1), 20 μM to 2 mM for the above (2), 4 μM to 1 mM for the above (3) and 10 μM to 2 mM for the above (4) are respectively preferable.

The chemical luminous reaction is carried out under the co-existence of the substances in the above (1)–(4), and usually the chemical luminous reaction is conducted by adding a solution containing any one among the above (1)–(4) into a system which contains the remaining three of the above (1)–(4). The luminous quantum produced in the reaction solution can be measured by a measuring instrument which is marketed or one's own made (e.g., a photocounter equipped with a high sensitive photoelectron multiplicator). That is, a quantitative analysis can be conducted by measuring luminous quantum in term of few seconds to few minutes at the stage of few seconds to several tens of minutes after the addition of the last solution.

Namely, a reliable relationship between the luminous quantum actually measured and the amount of the peroxidase can be recognized, based on which the analysis is possible. Usually, the peroxidase makes a co-valent bond with an immunochemically active substance.

Test sample to be analyzed may be bioliquids such as blood serum, blood plasma, urine, medullary liquid, etc., a liquid extracted from organ, or the like.

The chemical luminous quantum can be measured by a known method, for example, by a marketed or one's own made luminometer equipped with a photoelectron multiplicator. In case such an instrument is used, the luminous quantum produced in a few seconds to several tens of seconds after a few seconds to several hundred seconds from mixing of the above reagents is measured.

The compounds represented by the formula (I) can be prepared by an appropriate known method. The methods for preparing thiazole, oxazole or imidazole derivatives are well known in this field, and can be referred to the standard methods described in, for example, "Shin-Jikken-Kagaku-Koza", Vol. 14, Synthesis and Reaction of Organic Compounds [IV] (1978) published by Maruzen Co., Ltd. of Japan. The methods for preparing the compounds of the formula (I) are explained in detail in the following.

Method A
Step 1

(II)                                    (IV)

Step 2

(I-1)

In the formula, $R_6$ and $R_8$ are each hydrogen atom, a hydrocarbon residue which may be substituted or a heterocyclic group, $R_7$ is a phenyl group having a hydroxy group at the 4th position, or $R_7$ and $r_6$ are combined to form a group of the formula:

(wherein $R^9$ is a lower alkoxy or aralkyloxy), or $R^6$ and the 4-hydroxyphenyl group are combined to form a group of the formula:

X is an oxygen atom or a sulfur atom, and Y is a removable group.

The hydrocarbon residue which may be substituted and the heterocyclic group represented by $R_6$ and $R_8$ are the same as exemplified for $R_2$ and $R_3$. The phenyl group having a protected hydroxy group at the 4th position represented by $R_7$ may be 4-lower alkoxyphenyl such as 4-methoxyphenyl, 4-ethoxyphenyl, 4-isopropoxyphenyl, etc., or 4-aralkyloxyphenyl such as 4-benzyloxyphenyl, 4-(4-chlorobenzyloxy)phenyl, etc. The lower alkoxy for $R_9$ may be methoxy, ethoxy, propoxy, isopropoxy, butoxy, etc., and the aralkyloxy for $R_9$ may be benzyloxy, phenethyloxy, 4-chlorobenzyloxy, etc. The removable group for Y may be halogen (e.g., chlorine, bromine, iodine, etc.), methanesulfonyloxy, benzenesulfonyloxy, p-toluenesulfonyloxy, or the like.

Step 1

In this method, a compound (II) and a thioamide or amide derivative of the general formula (III) are reacted at first to give a thiazole or oxazole derivative (IV). This reaction (Step 1) is carried out in an appropriate solvent (e.g., toluene, xylene, pyridine, 1,2-dichloroethane, 1,1,2,2-tetrachloroethane, N,N-dimethylformamide, dimethyl sulfoxide, ethanol, etc.) or without solvent, by heating at 50° to 200° C. The amount of the compound (III) to be used is 1 to 10 moles, preferably 1.5 to 4 moles, to one mole of the compound (II). The reaction time is 0.5 to 30 hours, preferably 1 to 5 hours.

Step 2

The compound (IV) obtained in the above Step 1 is then subjected to removal reaction of the protective group to give a compound (I-1). This reaction for removing the protecting group is conducted by using an inorganic acid such as hydrobromic acid, hydrochloric acid or sulfuric acid, Lewis acid such as aluminum chloride, etc., pyridine hydrochloride, or the like. This reaction is preferably carried out by catalytic hydrogenation when $R_7$ is a benzyloxy derivative. In case the inorganic acid is used, alcohol (e.g., ethanol, propanol, ethyleneglycol, 2-methoxyethanol, etc.), water or a mixture thereof is used as a solvent. The inorganic acid is usually used in large excess (5 to 100 equivalents) for the compound (IV), preferably 10 to 50 equivalents. The reaction is carried out at 50° to 150° C. for 0.5 to 20 hours. The reaction for removing the protecting group by using Lewis acid is conducted in an appropriate inert solvent against Lewis acid (e.g., chloroform, dichloromethane, benzene, carbon disulfide, etc.) at −10° to 100° C. The amount of the Lewis acid to be used is 1 to 5 moles, preferably 1 to 3 moles to one mole of the compound (IV). The reaction time is 0.5 to 10 hours. The reaction using pyridine hydrochloride is carried out by heating a mixture of the compound (IV) and pyridine hydrochloride at 50° to 200° C. The amount of the pyridine hydrochloride to be used is 1 to 5 moles, preferably 1 to 3 moles, to one mole of the compound (IV). The reaction time is 0.5 to 10 hours.

Method B
Step 1

Step 2

Step 3

(I-2)

[wherein, $R_6$, $R_7$ and $R_8$ are each as defined in the above]

Step 1

In this method, a compound (VI) is at first acylated to give a compound (VII). The acylation reaction can be carried out by a known method, for example, in a proper solvent (e.g., chloroform, dichloromethane, ethyl acetate, tetrahydrofuran, water or a mixture thereof), in the presence of a base (e.g., triethylamine, N-methylmorpholine, sodium bicarbonate, potassium bicarbonate, sodium carbonate, potassium carbonate, etc.), at $-10°$ to $+50°$ C. for 0.1 to 5 hours. The amount of the compound (VI) to be used is 1 to 1.2 moles to one mole of the compound (V).

Step 2

Thus prepared compound (VII) is then reacted with a cyclizing agent containing nitrogen atom(s) such as urea or ammonia to give an oxazole derivative (VIII). In case ammonia is used as a reagent, the reagent is preferably in a form of an ammonium salt, for example, in a form of acetate in acetic acid. This reaction is carried out, for example, by heating a compound (VII) with 1 to 5 equivalents of ammonium acetate in acetic acid at 50° to 110° C. for 0.5 to 10 hours.

Step 3

Thus prepared compound (VIII) is then subjected to removing reaction of the protective group to give a compound (I-2). The removing reaction of the protective group can be carried out in the same manner as the Step 2 in the Method A.

Method C
Step 1

[wherein, $R_6$ and $R_7$ have the same meanings as defined above]

Step 1

In this process, a compound (V) is acylated by phenyl chlorocarbonate to give a compound (IX) at first. The acylation reaction can be conducted by a known method, for example, in a proper solvent (e.g., chloroform, dichloromethane, ethyl acetate, tetrahydrofuran, water or a mixture thereof), in the presence of a base (e.g., triethylamine, N-methylmorpholine, sodium bicarbonate, potassium bicarbonate, sodium carbonate, potassium carbonate, etc.), at $-10°$ to 50° C., for 0.1 to 5 hours. The amount of phenyl chlorocarbonate to be used is 1 to 1.2 moles to one mole of the compound (V).

Step 2

The compound (IX) is then reacted with a cyclizing agent containing nitrogen atom(s) such as urea or ammonia to give an oxazolone derivative (X). In case ammonia is used, the reagent is preferably in a form of ammonium, for example, in a form of acetate in acetic acid. This reaction is carried out, for example, by heating a compound (IX) with 1 to 5 equivalents of ammonium acetate in acetic acid at 50° to 110° C. for 0.5 to 10 hours.

Step 3

The compound (X) is then derived to a 2-chlorooxazole derivative (XI) by a known reaction using phosphorus oxychloride-N,N-dimethyl formamide (Vilsmeyer reagent), phosphorus pentoxide, or the like.

Step 4

The compound (XI) is then subjected to a reaction for removing the protective group to give a compound (I-3). The reaction for removing the protective group can be conducted in the same manner as the Step 2 in the Method A.

Method D $$R_4 \underset{H}{\overset{N}{\underset{X}{\bigvee}}} \underset{R_2}{\overset{R_4}{\underset{}{\bigvee}}} \longrightarrow R_4 \underset{Z}{\overset{N}{\underset{X}{\bigvee}}} \underset{R_2}{\overset{}{\underset{}{\bigvee}}}$$

(I-4)          (I-5)

[wherein, $R_2, R_4$ and X have the same meanings as above, and Z is a halogen atom]

In this method, a compound (I-4) having a hydrogen atom for $R_3$ in the general formula (I) is halogenated to give a compound (I-5) having a halogen atom (e.g., chlorine, bromine, iodine) for $R_3$. The halogenating reaction can be carried out by a known method, for example, in an inert solvent under the halogenating reaction conditions (e.g., chloroform, dichloromethane, carbon tetrachloride, tetrahydrofuran or a mixture thereof), in the presence of chlorine, bromine or iodine, at 0° to 100° C. for 0.1 to 5 hours. The amount of the chlorine, bromine or iodine to be used is 1 to 5 moles, preferably 1.2 to 3 moles for 1 mole of the compound (I-4).

Among the compounds represented by the general formula (I), the compounds having an imino group substituted by 4-hydroxyphenyl for $R_1$ can be synthesized by a method described in Journal of American Chemical Society Vol. 71, page 383 (1949).

In a luminescence system consisting of chemically luminous substance, oxidizing agent and peroxidase, the luminescence reaction can be delayed and the luminescence can be extremely enhanced by using a kind of the compounds (I) or a mixture thereof.

The following Preparations and Examples are given for illustrating the present invention in more detail, but it should be noted that the scope of this invention is not restricted to these Preparations and Examples.

REFERENCE EXAMPLE 1

Synthesis of 4-(4-hydroxyphenyl)thiazole (1) 4'-Benzyloxyacetophenone

4'-Hydroxyacetophenone (40g) and potassium carbonate (60.9 g) were mixed in dimethyl formamide (250 ml). Benzyl bromide (36.7 ml) was added dropwise to the mixture, and the mixture was stirred at room temperature for 1 hour and further at 50° to 60° C. for 1 hour. The reaction mixture was poured into ice-water, and the precipitating crystals were collected by filtration and recrystallized from methanol to give 4'-benzyloxyacetophenone (55.4g, 83.3%). m.p. 93°-94° C.
NMR(CDCl$_3$)δ: 2.5(3H,s), 5.1(2H,s),
6.97(2H,d,J=9 Hz), 7.36(5H,m),
7.17(2H,d,J=9 Hz)

(2) 4'-Benzyloxy-2-bromoacetophenone

4'-Benzyloxyacetophenone (55.0 g) was stirred in chloroform (500 ml), and bromine (13.0 ml) was added dropwise thereto at room temperature in 30 minutes. The mixture was stirred for 10 minutes, and the reaction mixture was washed with aqueous solution of sodium sulfate, water and saturated saline in turn, dried with anhydrous sodium sulfate and then concentrated. The precipitating crystals were recrystallized from acetone-diisopropyl ether to give 4'-benzyloxy-2-bromoacetophenone (25.7 g, 34.6%). m.p. 81°-82° C.
NMR(CDCl$_3$)δ: 4.4(2H,s), 5.1(2H,s),
7.0(2H,d,J=9 Hz), 7.4(5H,m),
7.95(2H,d,J=9 Hz)

(3) Thioformamide

Phosphorus pentasulfide (5 g) was added slowly to formamide (10 g) in 20 minutes under stirring and ice-cooling. After stirring at room temperature for 1 hour, diethyl ether (75 ml) was added thereto, and the mixture was stirred for 20 hours. The ether layer was concentrated to give oily product (5.2 g, 38.2%). The product was purified by column chromatography on silica gel [eluting solvent: ethyl acetate-hexane (1:1)] to give thioformamide (1.65 g).

(4) 4-(4-Benzyloxyphenyl)thiazole

A mixture of 4'-benzyloxy-2-bromoacetophenone (3.0 g) and thioformamide (0.63 g) in ethanol (50 ml) was refluxed under heating for 30 minutes. The reaction mixture was poured into ice-water, and the precipitating crystals were collected by filtration, extracted with diethyl ether and purified by column chromatography on silica gel [eluting solvent: methylene chloride-hexane (1:9)] to give 4-(4-benzyloxyphenyl) thiazole (720 mg, 27.7%), which was further purified by recrystallization from diethyl ether-hexane. m.p. 109°-110° C.
NMR(CDCl$_3$)δ: 5.1(2H,s), 7.0(2H,d,J=9 Hz),
7.4(1H,d,J=2 Hz), 7.4(5H,m),
7.85(2H,d,J=9 Hz), 8.8(1H,d,J=2 Hz)
IR(KBr) : 1610 cm$^{-1}$
Elementary analysis: C$_{16}$H$_{13}$NOS:
Calculated: C, 71.88; H, 4.90; N, 5.24.
Found : C, 71.94; H, 4.85; N, 5.07.

(5) 4-(4-Hydroxyphenyl)thiazole

To 4-(4-benzyloxyphenyl)thiazole (1.1 g) was added 47% aqueous hydrogen bromide (10ml), and the mixture was stirred at 100° C. for 30 minutes. Ice-water was added to the reaction mixture and extracted with ethyl acetate. The ethyl acetate layer was washed with saturated saline, dried by anhydrous sodium sulfate and then concentrated. Crystals were collected by filtration by using hexane to give 4-(4-hydroxyphenyl) thiazole (466 mg, 63.8%). The crystals were purified by recrystallization from methylene chloride-hexane. m.p. 161.5°-162° C.
NMR(CDCl$_3$)δ: 5.4(1H,s), 6.85(2H,d,J=9 Hz),
7.35(1H,d,J=2 Hz), 7.8(2H,d,J=9 Hz),
8.8(1H,d,J=2 Hz)
IR(KBr) : 1610, 3100 cm$^{-1}$
Elementary analysis: C$_9$H$_7$NOS
Calculated: C, 60.99; H, 3.98; N, 7.90.
Found : C, 61.00; H, 3.85; N, 7.78.

REFERENCE EXAMPLE 2

Synthesis of 4-(4-hydroxyphenyl)oxazole (1) 4-(4-Benzyloxyphenyl)oxazole

Formamide (1.0ml) was added to 4'-benzyloxy-2-bromoacetophenone (3.0g) and heated at 130° to 135° C. for 1 hour. Water was added to the reaction product, and the mixture was alkalified with aqueous solution of sodium bicarbonate and then extracted with ethyl acetate. The ethyl acetate layer was washed with saturated saline, treated with activated charcoal, dried with anhydrous sodium sulfate and then concentrated. The residue was purified by column chromatography on silica gel [eluting solvent: ethyl acetate-hexane (1:9)] to give 4-(4-benzyloxyphenyl) oxazole (410 mg, 16.6%). The product was further purified by recrystallization from diethyl etherhexane. m.p. 101°-102° C.

NMR(CDCl$_3$)δ: 5.1(2H,s), 7.0(2H,d,J=9 Hz), 7 4(5H,m), 7.7(2H,d,J=9 Hz), 7.8(1H,s), 7.9(1H,s)

(2) 4-(4-Hydroxyphenyl)oxazole 4-(4-Benzyloxyphenyl)oxazole (360mg) was dissolved in methanol (10 ml). 5% Palladium on carbon (containing 50% water) (300 mg) was added to the solution, and the mixture was subjected to catalytic reduction for 80 minutes. The catalyst was filtered off from the reaction mixture, and the filtrate was concentrated. The residue was purified by column chromatography on silica gel [eluting solvent: ethyl acetate-hexane (1:2)] to give 4-(4-hydroxyphenyl)oxazole (105 mg, 45.5%). The product was further purified by recrystallization from diethyl ether-hexane. m.p. 147.5°-148° C.

NMR(CDCl$_3$)δ: 5.7(1H,s), 6.9(2H,d,J=9 Hz), 7.7(2H,d,J=9 Hz), 7.9(1H,s), 8.0(1H,s)
IR(KBr) : 3350, 3130$^{-1}$
Elementary analysis: C$_9$H$_7$NO$_2$:
Calculated: C, 67.08; H, 4.38; N, 8.69.
Found : C, 67.06; H, 4.42; N, 8.57.

EXAMPLE 1

Reagent

Sodium luminol was used after recrystallization from aqueous sodium hydroxide. Horseradish peroxidase (HRP) Type VI manufactured by Sigma Chemical was used.

Analysis equipment

Chemical luminescence reaction was conducted in a disposable glass culture tube (12mm×75mm, manufactured by Corning). The luminescence was measured by using a luminometer (BLR-201, manufactured by Aloka).

1 Screening of enhancer

Luminol solution was prepared by adding sodium luminol (12.5 mg) and aqueous hydrogen peroxide (15 μl 31%) to borate buffer (0.2 molarity, pH 8.5, 50 ml). HRP solution was prepared by diluting HRP with borate buffer (0.2 molarity, pH 8.5). Both solutions were prepared about 2 hours before the use and cooled with ice.

A solution (10 μl ) of a sample as an enhancer in dimethylsulfoxide was added to a luminol solution (990 μl) just before the use and mixed. The mixture (100 μl ) of luminol/hydrogen peroxide/enhancer and HRP solution (1ng/ml, 100 μl ) were mixed in a culture tube, and improvement of ratio of signal/background at 5 minutes later was measured. The results are shown in the following Table 1.

TABLE 1

| Enhancer sample | Additive concentration (mM) | Improvement of ratio of signal/background |
|---|---|---|
| P-iodophenol* (manufactured by Wako Pure Chemical Industries, Ltd.) | 40 | 72.0 |
|  | 4 | 5.3 |
|  | 0.4 | 1.0 |

TABLE 1-continued

| Enhancer sample | Additive concentration (mM) | Improvement of ratio of signal/background |
|---|---|---|
| 4-(4-hydroxyphenyl) oxazole (Reference Example 2) | 40 | 12.8 |
|  | 4 | 49.7 |
| 4-(4-hydroxyphenyl) thiazole (Reference Example 1) | 40 | 163.3 |
|  | 4 | 403.1 |
| 2-ethyl-4-(4-hydroxyphenyl)-5-(3-pyridyl) thiazole | 40 | 381.3 |
|  | 4 | 46.1 |
| 4-(imidazol-1-yl) phenol | 40 | 110.3 |
|  | 4 | 6.0 |
|  | 0.4 | 1.3 |
| 4-(4-hydroxyphenyl)-2-methylthiazole (Reference Example 2) | 40 | 10.7 |
|  | 4 | 119.2 |
| 4-(4-hydroxyphenyl)-5-(3-pyridyl) thiazole | 40 | 146.4 |
|  | 4 | 21.4 |
| 4-(4-hydroxyphenyl)-2-(3-pyridyl) thiazole | 40 | 33.5 |
|  | 4 | 87.5 |
| 4-(4-hydroxyphenyl)-2-(4-pyridyl) thiazole | 40 | 10.8 |
|  | 4 | 44.8 |
| 2-amino-4,5-dihydro-naptha[1,2-d]thiazole | 40 | 0.3 |
|  | 4 | 5.0 |
|  | 0.4 | 8.0 |

*control enhancer

2 Measurement for curve relating to amount and activity

Luminol solution was prepared by adding sodium luminol (5mg) and aqueous hydrogen peroxide (12 μl, 31%) to borate buffer (0.2 molarity, pH 8.5, 50 ml). HRP solution was prepared by diluting HRP with borate buffer (0.2 molarity, pH 8.5). These solutions were prepared about 2 hours before the use and cooled with ice.

A solution (10 μl ) of a sample as an enhancer in dimethyl sulfoxide was added to a luminol solution (990 μl ) just before the use and mixed. [p-indophenol 40 mM, 4-(4-hydroxyphenyl)oxazole 4 mM, 4-(4-hydroxyphenyl)thiazole 4 mM, 2-ethyl-4-(4-hydroxyphenyl)-5-(3-pyridyl)thiazole 40mM were used, respectively.] The mixture (100 μl ) of luminol/hydrogen peroxide/enhancer and HRP solution diluted in 10 stages (0-10ng/ml) (100 μl ) were mixed in a culture tube, and the signal at 5 minutes later was measured. The results are shown in the following Table 2.

TABLE 2

| HRP (pg/ml) | Sample of Enhancer | | | |
|---|---|---|---|---|
|  | (1) | (2) | (3) | (4) |
| 0 | 63 | 28 | 99 | 99 |
| 0.01 | 73 | 25 | 90 | 38 |
| 0.1 | 63 | 28 | 97 | 38 |
| 1 | 74 | 30 | 122 | 37 |
| 10 | 80 | 85 | 241 | 49 |
| 10$^2$ | 323 | 192 | 1,044 | 506 |
| 10$^3$ | 8,738 | 3,427 | 19,832 | 14,641 |
| 10$^4$ | 108,089 | 51,896 | 120,041 | 139,346 |

Figure 1:
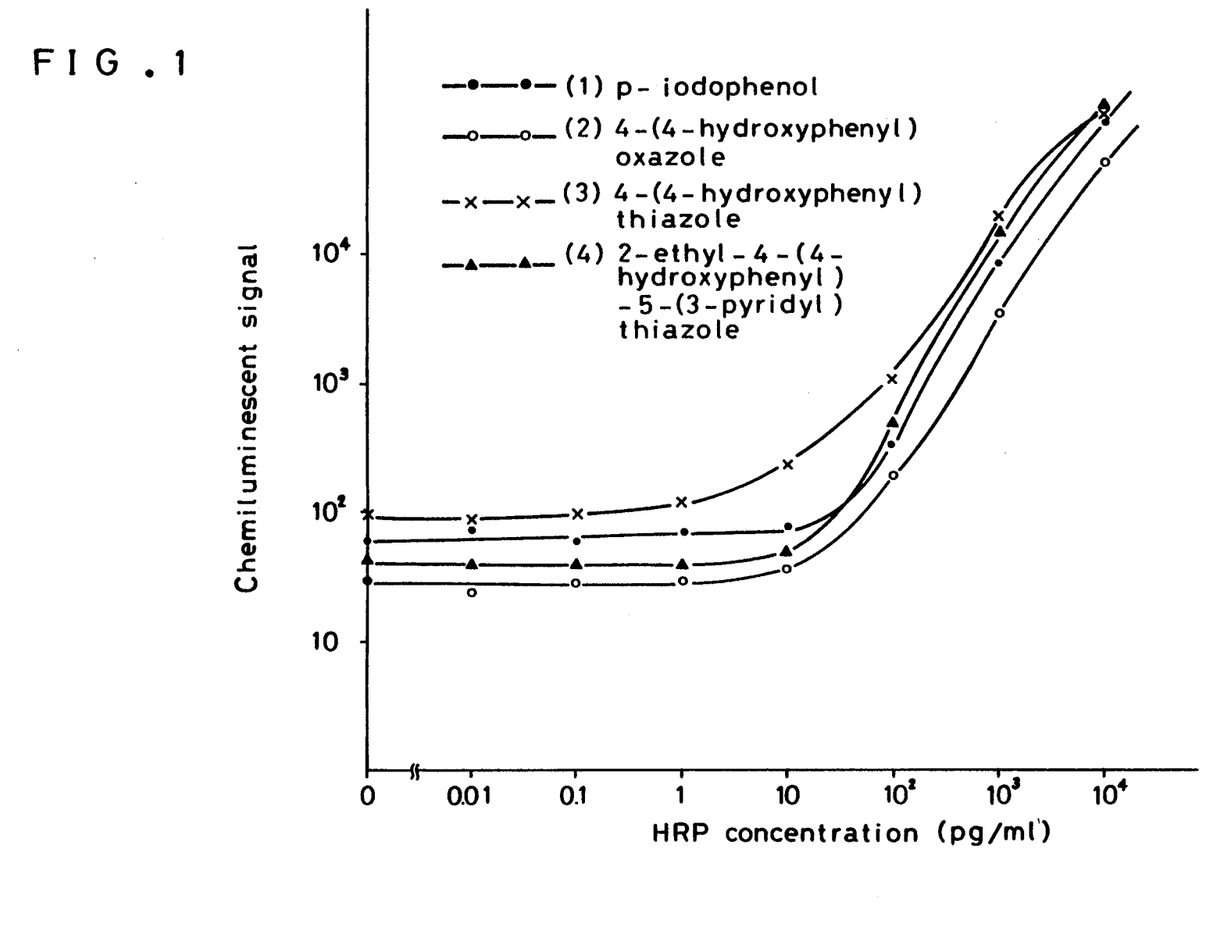
FIG. 1 shows a relation between the chemiluminescent signal and HRP concentration.

Sample of enhancer
(1): p-iodophenol
(2): 4-(4-hydroxyphenyl)oxazole
(3): 4-(4-hydroxyphenyl)thiazole
(4): 2-ethyl-4-(4-hydroxyphenyl)-5-(3-pyridyl) thiazole The relation between the HRP concentration and the signal are shown in FIG. 1.

The limits for detecting HRP by using each of these compounds were judged from FIG. 1, and the results are shown in the following.

| (1) | p-iodophenol | 50 pg/ml |
|---|---|---|
| (2) | 4-(4-hydroxyphenyl)oxazole | 10 pg/ml |
| (3) | 4-(4-hydroxyphenyl)thiazole | 5 pg/ml |
| (4) | 2-ethyl-4-(4-hydroxyphenyl)-5-(3-pyridyl)thiazole | 10 pg/ml |

EXAMPLE 2

Measurement for hCG

1. Purification of anti-hCG-$\beta$-CTP (1) Saturated aqueous solution of ammonium sulfate (3.3 ml) was added to rabbit antiserum (5 ml) which was rendered immune by P1 peptide [hCG-$\beta$C end peptide (123-145)], and the mixture was stirred at room temperature. After centrifuging at 10,000 rpm for 10 minutes, precipitate was dissolved in saline (5 ml).

(2) Saturated aqueous solution of ammonium sulfate (2.7 ml) was added to the solution, and the mixture was stirred at room temperature for 30 minutes and centrifuging at 10,000rpm for 10 minutes. Precipitate was dissolved in saline (5 ml).

(3) The solution was dialyzed with 0.02M borate buffer (pH 8.0) overnight and centrifuged at 10,000 rpm for 10 minutes to remove the precipitate.

(4) The solution was subjected to an affinity column on P1 peptide solidified on sepharose 4B. The dialyzed substance was put on the column, washed with 0.02M borate buffer (pH 8.0) and then with 0.17M glycine buffer (pH 3.0), and eluted with 3M sodium thiocyanate buffer (pH 7.4).

(5) Eluate fractions were collected, and dialyzed with saline (containing 0.01% sodium azide) overnight to give an anti-hCG-$\beta$-CTP solution. Absorption at 280nm was measured and protein concentration was determined to 219.2 $\mu$g/ml and the total amount to 1.64 mg.

2. Preparation of anti-hCG-$\beta$-CTP solidified on polystyrene beads (1) Polystyrene beads (4.4 mm diameter) were stirred in 2N aqueous sodium hydroxide for 2 hours, washed with distilled water and then dried. The beads were stirred in 2N hydrochloric acid for 2 hours, washed with distilled water and then dried.

(2) Anti-hCG-$\beta$-CTP was dissolved in 0.1M carbonate buffer (pH 9.5). Polystyrene beads were added to the solution and allowed to stand at 4° C. for 3 days (1 $\mu$g of anti-hCG-$\beta$-CTP 1 $\mu$g/per one piece of polystyrene bead).

(3)The beads were washed with saline. 1% BSA solution was added to the beads and the mixture was allowed to stand at 4° C. for 1 day.

(4) The beads were washed with saline and stored at 4° C. in 0.1% BSA solution.

3. Measurement (1) Each sample (100 $\mu$l) containing various amount of hCG and 0.02M phosphate buffer (containing 10% calf serum) (100 $\mu$l) were mixed. Anti-hCG-$\beta$-CTP solidified on polystyrene beads were added to the mixture and allowed to stand at room temperature overnight.

(2) The beads were washed with distilled water. Diluted solution of anti-hCG/HRP compound (200 $\mu$l was added to the beads, and the mixture was allowed to stand at room temperature for 2 hours.

(3) The beads were washed with distilled water and put in a test tube for measuring the luminescence. A solution containing luminol (100 $\mu$M), hydrogen peroxide (300 $\mu$M) and enhancer, 4-(4-hydroxyphenyl) thiazole (40 $\mu$M) was added to the beads, and the luminous reaction was started. Luminous quantum at 1 minute later was measured Limits for detecting hCG was 0.005 mIU/ml.

EXAMPLE 3

Measurement for Endothelin

Procedure

Determined wells of Microtiter plate with 96 wells (DYNATECH micro FLUOR ®, Dynatech Lab. Ltd., Chantilly, Va. USA) were coated with monoclonal anti-endothelin antibody as described in Suzuki et al., J. Immun. Methods 118, 245-250 (1989).

One hundred $\mu$l of a solution of emdothelin (1-21, Peptide Institute Inc., Osaka, Japan) (0, 0.2, 0.5 and 1 pg/me) in 0.02M phosphate buffer (pH 7.0) containing 10% Block Ace ® (Snow Brand Milk Products Co., Ltd., Japan), 0.4M NaCl and 1 mM EDTA were added to the wells of the plate and incubated for 16 hours at 6° C. The wells were washed with 0.05M phosphate buffer containing 0.8% NaCl. Then, 100 $\mu$l of a solution of polyclonal anti- endothelin antibody-HRP complex (see the above Suzuki et al.) were added to each well of the plate. The plate was incubated for 24 hours at 6° C. and washed with a phosphate buffer. Then, HRP activity present in the plate was measured by a chemiluminescence method using an enhancer of the present invention. That is, 100 $\mu$l of 0.1M Tris buffer (pH 8.7) containing 2 mM luminol, 500 $\mu$M $H_2O_2$ and 20 $\mu$M 4-(4-hydroxyphenyl) thiazole, 0.25% ethanol and 0.02 mM EDTA were added to each well of the plate, and the light was measured on an automated microtiter plate chemiluminescence machine (Model ML 1000, Dynatech Lab. Inc.) adjusted for high sensitivity and 0.25 second measurements.

The detection limit was 0.03 pg of endothelin, and thus the method of the present invention can be said to show every high sensitivity.

What we claim is:

1. In a method for enhancing chemiluminescence, the improvement comprising using in a luminescence system which contains at least one member selected from the group consisting of a chemically luminous substance, and oxidizing agent and a peroxidase; a compound of the formula (I):

wherein
$R_1$ is oxygen or sulfur, $R_2$ and $R_3$ are the same or different and are selected from the group consisting of
hydrogen,
halogen,
a hydrocarbon group selected from the group consisting of (a) a $C_{1-10}$ alkyl group, (b) a $C_{2-10}$ alkenyl group, (c) a $C_{6-14}$ aryl group and (d) a $C_{7-19}$ aralkyl group, wherein the hydrocarbon group may be substituted with 1 to 3 substituent(s) selected from the group consisting of a halogen, a hydroxy group, a $C_{1-6}$ alkoxy group, an amino group optionally substituted with a $C_{1-6}$ alkyl, an amino group substituted with a $C_{1-10}$ alkanoyl group, a carbamoyl group optionally substituted with a $C_{1-6}$ alkyl group, a mono- or di-alkoxyphosphoryl group, a $C_{1-6}$ alkoxycarbonyl group, a $C_{6-14}$ aryloxycarbonyl group and a $C_{7-19}$ aralkyloxycarbonyl group, and a pyridyl group which may be substituted with a substituent selected from the group consisting of a halogen, a $C_{1-6}$ alkyl group, a halogenated $C_{1-6}$ alkyl group, hydroxy group, a $C_{1-6}$ alkoxy group, a $C_{1-10}$ acyl group, an amino group which may be substituted by a $C_{1-6}$ alkyl or $C_{1-10}$ acyl, a carbamoyl group which may be substituted by a $C_{1-6}$ alkyl, and a $C_{1-6}$ alkoxycarbonyl group, and $R_4$ is a 4-hydroxyphenyl group.

2. A method of claim 1 in which the compound (I) is a compound of the formula:

wherein $R_1$, $R_2$ and $R_3$ have the same meanings as defined in claim 1.

3. A method of claim 1 in which the chemically luminous substance is luminol.

4. A method of claim 1 in which the peroxidase is coupled to an immunochemically active substance.

5. A method of claim 1 in which the compound (I) is 4-(4-hydroxyphenyl)thiazole.

6. A method of claim 1 in which the compound (I) is 4-(4-hydroxyphenyl)-2-methylthiazole.

7. A method of claim 1 in which the compound (I) is 4-(4-hydroxyphenyl)-2-(3-pyridyl)thiazole.

8. A method of claim 1, wherein the luminescence system contains luminol.

9. A method of claim 1, wherein the luminescence system contains horseradish peroxidase.

10. A method of claim 1 wherein $R_1$ is sulfur.

11. A combination which comprises as elements a chemically luminous substance, an oxidizing agent a peroxidase and said compound of formula (I) as defined in claim 1.

12. A combination comprising a group of ingredients for an assay determination which comprises as elements a chemically luminous substance, an oxidizing agent, a peroxidase and said compound of formula (I) as defined in claim 1 said elements being in uncombined form until said assay determination is carried out.

* * * * *